United States Patent
Chien

(10) Patent No.: US 10,605,957 B2
(45) Date of Patent: Mar. 31, 2020

(54) GAS PERMEABLE OPHTHALMIC LENS MATERIAL AND GAS PERMEABLE OPHTHALMIC LENS OF SUCH MATERIAL

(71) Applicant: ScienBiziP Consulting(Shenzhen)Co., Ltd., Shenzhen (CN)

(72) Inventor: Hsiu-Wen Chien, New Taipei (TW)

(73) Assignee: ScienBiziP Consulting(Shenzhen)Co., Ltd., Shenzhen (CN)

( * ) Notice: Subject to any disclaimer, the term of this patent is extended or adjusted under 35 U.S.C. 154(b) by 288 days.

(21) Appl. No.: 15/786,025

(22) Filed: Oct. 17, 2017

(65) Prior Publication Data
US 2019/0094416 A1   Mar. 28, 2019

(30) Foreign Application Priority Data

Sep. 26, 2017   (TW) ............................. 106132951 A

(51) Int. Cl.
| | |
|---|---|
| *G02B 1/04* | (2006.01) |
| *C08L 83/04* | (2006.01) |
| *C07F 7/04* | (2006.01) |
| *C08G 77/26* | (2006.01) |
| *C08L 83/08* | (2006.01) |
| *C08G 77/28* | (2006.01) |
| *C08G 77/30* | (2006.01) |

(52) U.S. Cl.
CPC .............. *G02B 1/043* (2013.01); *C07F 7/045* (2013.01); *C08G 77/26* (2013.01); *C08G 77/28* (2013.01); *C08G 77/30* (2013.01); *C08L 83/04* (2013.01); *C08L 83/08* (2013.01)

(58) Field of Classification Search
CPC ......... G02B 1/043; C07F 7/045; C08G 77/26; C08G 77/28; C08G 77/30; C08G 183/04; C08G 183/08
USPC ........... 351/159.01, 159.02, 159.33; 623/4.1, 623/6.53; 556/400, 465
See application file for complete search history.

(56) References Cited

U.S. PATENT DOCUMENTS

| | | | |
|---|---|---|---|
| 2008/0312182 A1* | 12/2008 | Burke | ................... A61L 12/142 514/54 |
| 2009/0030108 A1* | 1/2009 | Ito | ........................... A61L 27/18 523/106 |
| 2014/0017121 A1* | 1/2014 | Schoenfisch | .......... C07F 7/0874 422/22 |

OTHER PUBLICATIONS

Modification of Silicone Elastomer with Zwitterionic Silane for Durable Antifouling Properties, Yeh et al., Langmuir 2014, 30, 11386-11393 (Year: 2014).*

* cited by examiner

*Primary Examiner* — Travis S Fissel
(74) *Attorney, Agent, or Firm* — ScienBiziP, P.C.

(57) ABSTRACT

A gas permeable ophthalmic lens material comprises a tetraethoxysilane and an ionic silane. The ionic silane comprises positive charges and negative charges. The lens made therefrom thus comprises positive and negative charges, thus the gas permeable ophthalmic lens is hydrophilic, and prevents adhesion of bacteria in allowing the surface of the human eye to breath. A gas permeable ophthalmic lens made of the gas permeable ophthalmic lens material is also provided.

6 Claims, 1 Drawing Sheet

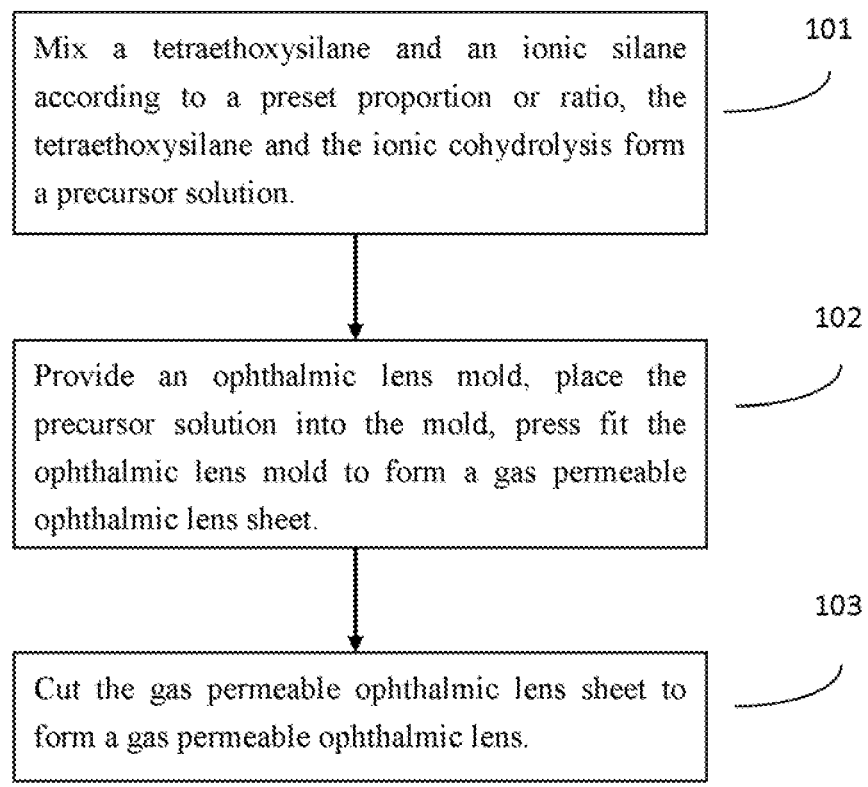

GAS PERMEABLE OPHTHALMIC LENS MATERIAL AND GAS PERMEABLE OPHTHALMIC LENS OF SUCH MATERIAL

FIELD

The subject matter generally relates to eye-health technology, and particularly to a gas permeable ophthalmic lens material and a gas permeable ophthalmic lens.

BACKGROUND

Ophthalmic lenses are worn by users to correct vision, or for cosmetic or therapeutic reasons. Since the ophthalmic lens directly contacts eyes of the user when in use, ophthalmic lens that allow oxygen and other gas to pass through is needed.

BRIEF DESCRIPTION OF THE DRAWING

Implementations of the present disclosure will now be described, by way of example only, with reference to the attached FIGURE.

FIG. 1 is a flowchart of an exemplary embodiment of a method for manufacturing a gas permeable ophthalmic lens.

DETAILED DESCRIPTION

It will be appreciated that for simplicity and clarity of illustration, where appropriate, reference numerals have been repeated among the different figures to indicate corresponding or analogous elements. In addition, numerous specific details are set forth to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale, and the proportions of certain parts may be exaggerated to illustrate details and features of the present disclosure better. The disclosure is illustrated by way of example and not by way of limitation in the figures of the accompanying drawings, in which like references indicate similar elements. It should be noted that references to "an" or "one" embodiment in this disclosure are not necessarily to the same embodiment, and such references mean "at least one."

The term "comprising" when utilized, means "including, but not necessarily limited to"; it specifically indicates open-ended inclusion or membership in the so-described combination, group, series, and the like.

An exemplary embodiment of a gas permeable ophthalmic lens material comprises a tetraethoxysilane (TEOS) and an ionic silane. The ionic silane comprises positive charges and negative charges.

In at least one exemplary embodiment, the ionic silane is a zwitterionic silane. In other exemplary embodiment, the ionic silane comprises a positively charged molecule silane and a negatively charged molecule silane.

When the ionic silane is a zwitterionic silane, the tetraethoxysilane has a mass percentage of about 68% to about 98.5% of the total mass of the gas permeable ophthalmic lens material. The zwitterionic silane has a mass percentage of about 1.5% to about 32% of the total mass of the gas permeable ophthalmic lens material.

The zwitterionic silane may be selected from sulfobetainesilane, carboxybetainesilane, phosphorylcholinesilane, or any combination thereof.

A chemical structure formula of the sulfobetainesilane is:

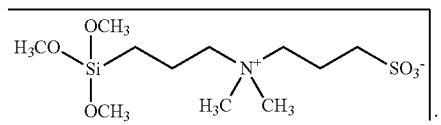

A chemical structure formula of the carboxybetainesilane is:

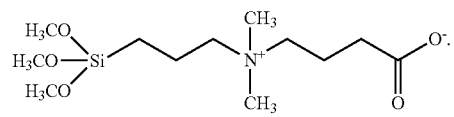

A chemical structure formula of the phosphorylcholinesilane is:

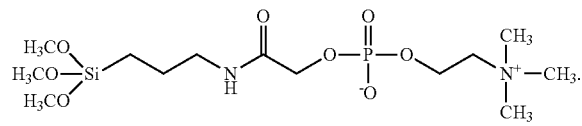

The zwitterionic silane has positive charge and negative charge. A total electrical charge of the zwitterionic silane is net zero. Thus, the zwitterionic silane is hydrophilic, and prevents adhesion of bacteria. Thus, the gas permeable ophthalmic lens material is hydrophilic, and prevents adhesion of bacteria.

When the ionic silane comprises the positively charged molecule silane and the negatively charged molecule silane, the tetraethoxysilane has a mass percentage of about 67.2% to about 98% of the total mass of the gas permeable ophthalmic lens material. The positively charged molecule silane has a mass percentage of about 0.8% to about 32% of the total mass of the gas permeable ophthalmic lens material, the negatively charged molecule silane has a mass percentage of about 0.8% to about 32% of the total mass of the gas permeable ophthalmic lens material.

The positively charged molecule silane may be selected from 3-(trimethoxysilyl)propyl-N,N,N-trimethylammonium, N-(trimethoxysilylpropyl) ethylenediaminetriacetate, 4-(TRIMETHOXYSILYLETHYL)BENZYLTRIMETHYLAMMONIUM CHLORIDE, TETRADECYLDIMETHYL(3-TRIMETHOXYSILYLPROPYL)AMMONIUM CHLORIDE, or any combination thereof.

The negatively charged molecule silane may be selected from carboxyethylsilanetriol, 3-(TRIHYDROXYSILYL)-1-PROPANESULFONIC ACID, TRIETHOXYSILYLPROPYLMALEAMIC ACID, 3-(TRIHYDROXYSILYL)PROPYL METHYLPHOSPHONATE, or any combination thereof.

The positively charged molecule silane has positive charge, the negatively charged molecule silane has negative charge, and a total electrical charge of the ionic silane is zero. Thus, the ionic silane is hydrophilic, and prevents adhesion of bacteria. Thus, the gas permeable ophthalmic lens material is hydrophilic, and prevents adhesion of bacteria.

An exemplary embodiment of a gas permeable ophthalmic lens formed by the gas permeable ophthalmic lens material is provided.

When the gas permeable ophthalmic lens material comprises zwitterionic silane, the gas permeable ophthalmic lens comprises following chemical structure:

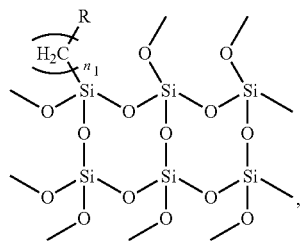

wherein, the R may be sulfobetainesilane group, carboxybetainesilane group, or phosphorylcholinesilane group. The $n_1$ is a positive integer. In the chemical structure, O— connects with Si, Si— connects with O, and is repeating, thus forming a continuous —Si—O— network structure.

A chemical structure formula of the sulfobetainesilane group is:

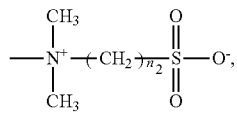

wherein, the $n_2$ may be 1, 2, or 3.

A chemical structure formula of the carboxybetainesilane group is:

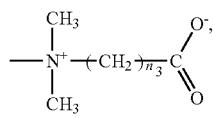

wherein, the $n_3$ may be 1, 2, or 3.

A chemical structure formula of the phosphorylcholinesilane group is:

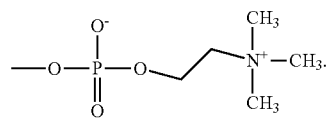

When the gas permeable ophthalmic lens material comprises the positively charged molecule silane and the negatively charged molecule silane, the gas permeable ophthalmic lens comprises following chemical structure:

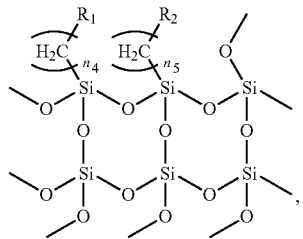

wherein, the $n_4$ is a positive integer, the $n_5$ is a positive integer. In the chemical structure, O— connects with Si, Si— connects with O, and is repeating, thus forming a continuous —Si—O— network structure. The $R_1$ is

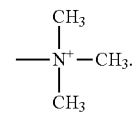

The $R_2$ may be

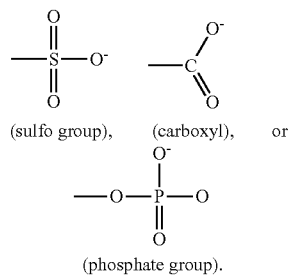

(sulfo group), (carboxyl), or (phosphate group).

The gas permeable ophthalmic lens comprises positive charges and negative charges, thus the gas permeable ophthalmic lens is hydrophilic, and prevents adhesion of bacteria.

FIG. 1 illustrates a flowchart of a method for making the gas permeable ophthalmic lens with an exemplary embodiment. The exemplary method is provided by way of example, as there are a variety of ways to carry out the method. Each block shown in the FIGURE represents one or more processes, methods, or subroutines, carried out in the exemplary method. Furthermore, the illustrated order of blocks is by example only and the order of the blocks can change. Additional blocks may be added or fewer blocks may be utilized, without departing from this disclosure. The exemplary method may begin at block 101.

At block 101, a tetraethoxysilane and an ionic silane are mixed according to a preset proportion or ratio, and the tetraethoxysilane and the ionic cohydrolysis form a precursor solution.

At block 102, an ophthalmic lens mold is provided, the precursor solution is placed into the mold, the ophthalmic lens mold is press fitted to form a gas permeable ophthalmic lens sheet.

At block 103, the gas permeable ophthalmic lens sheet is cut to form a gas permeable ophthalmic lens.

Example 1

The gas permeable ophthalmic lens material comprised tetraethoxysilane, and sulfobetainesilane.

The tetraethoxysilane had a mass percentage of 94.8% of the total mass of the gas permeable ophthalmic lens material, and the sulfobetainesilane had a mass percentage of 5.2% of the total mass of the gas permeable ophthalmic lens material.

The gas permeable ophthalmic lens made by the gas permeable ophthalmic lens material has a surface water contact angle of 60 degrees.

The gas permeable ophthalmic lens made by the gas permeable ophthalmic lens material has an oxygen permeability coefficient of 100.

Example 2

The gas permeable ophthalmic lens material comprised tetraethoxysilane, and carboxybetainesilane.

The tetraethoxysilane had a mass percentage of 90.2% of the total mass of the gas permeable ophthalmic lens material, the carboxybetainesilane had a mass percentage of 9.8% of the total mass of the gas permeable ophthalmic lens material.

The gas permeable ophthalmic lens made by the gas permeable ophthalmic lens material has a surface water contact angle of 46 degrees.

The gas permeable ophthalmic lens made by the gas permeable ophthalmic lens material has an oxygen permeability coefficient of 100.

Example 3

The gas permeable ophthalmic lens material comprised tetraethoxysilane, carboxyethylsilanetriol, and 3-(trimethoxysilyl)propyl-N,N,N-trimethylammonium.

The tetraethoxysilane had a mass percentage of 95% of the total mass of the gas permeable ophthalmic lens material, the carboxyethylsilanetriol had a mass percentage of 2.5% of the total mass of the gas permeable ophthalmic lens material, and the 3-(trimethoxysilyl)propyl-N,N,N-trimethylammonium had a mass percentage of 2.5% of the total mass of the gas permeable ophthalmic lens material.

The gas permeable ophthalmic lens made by the gas permeable ophthalmic lens material has a surface water contact angle of 58 degrees.

The gas permeable ophthalmic lens made by the gas permeable ophthalmic lens material has an oxygen permeability coefficient of 100.

Example 4

The gas permeable ophthalmic lens material comprised tetraethoxysilane, 3-(trimethoxysilyl)propyl-N,N,N-trimethylammonium, and N-(trimethoxysilylpropyl) ethylenediaminetriacetate.

The tetraethoxysilane had a mass percentage of 90% of the total mass of the gas permeable ophthalmic lens material, the 3-(trimethoxysilyl)propyl-N,N,N-trimethylammonium had a mass percentage of 7.5% of the total mass of the gas permeable ophthalmic lens material, and the N-(trimethoxysilylpropyl) ethylenediaminetriacetate had a mass percentage of 2.5% of the total mass of the gas permeable ophthalmic lens material.

The gas permeable ophthalmic lens made by the gas permeable ophthalmic lens material has a surface water contact angle of 52 degrees.

The gas permeable ophthalmic lens made by the gas permeable ophthalmic lens material has an oxygen permeability coefficient of 100.

It is to be understood, even though information and advantages of the present embodiments have been set forth in the foregoing description, together with details of the structures and functions of the present embodiments, the disclosure is illustrative only; changes may be made in detail, especially in matters of shape, size, and arrangement of parts within the principles of the present embodiments to the full extent indicated by the plain meaning of the terms in which the appended claims are expressed.

What is claimed is:

1. A gas permeable ophthalmic lens formed with:
   a gas permeable ophthalmic lens material, the gas permeable ophthalmic lens material comprising:
   tetraethoxysilane molecules; and
   ionic silane molecules;
   wherein the ionic silane molecules comprise positive charges and negative charges; the gas permeable ophthalmic lens comprises following chemical structure:

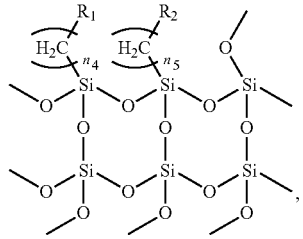

wherein, the $n_4$ is a positive integer, the $n_5$ is a positive integer, the $R_1$ is

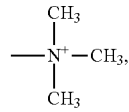

the $R_2$ is

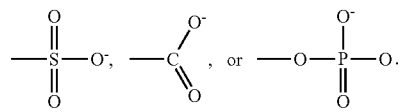

2. The gas permeable ophthalmic lens of claim 1, wherein the tetraethoxysilane molecules have a mass percentage of about 68% to about 98.5% of the total mass of the gas permeable ophthalmic lens material, the ionic silane molecules have a mass percentage of about 1.5% to about 32% of the total mass of the gas permeable ophthalmic lens material.

3. The gas permeable ophthalmic lens of claim 1, wherein the ionic silane molecules comprise silane molecules with positive charges and silane molecules with negative charges.

4. The gas permeable ophthalmic lens of claim 3, wherein the tetraethoxysilane molecules have a mass percentage of about 67.2% to about 98% of the total mass of the gas permeable ophthalmic lens material, the silane molecules with positive charges have a mass percentage of about 0.8% to about 32% of the total mass of the gas permeable ophthalmic lens material, the silane molecules with negative charges have a mass percentage of about 0.8% to about 32% of the total mass of the gas permeable ophthalmic lens material.

5. The gas permeable ophthalmic lens of claim 3, wherein the silane molecules with positive charges are selected from 3-(trimethoxysilyl)propyl-N,N,N-trimethylammonium, N-(trimethoxysilylpropyl) ethylenediaminetriacetate, 4-(trimethoxysilylethyl)benzyltrimethylammonium chloride, tetradecyldimethyl(3-trimethoxysilylpropyl)ammonium chloride, or any combination thereof.

6. The gas permeable ophthalmic lens of claim 3, wherein the silane molecules with negative charges are selected from carboxyethylsilanetriol, 3-(trihydroxysilyl)-1-propanesulfonic acid, triethoxysilylpropylmaleamic acid, 3-(trihydroxysilyl) propyl methylphosphonate, or any combination thereof.

\* \* \* \* \*